United States Patent
Rolland et al.

(10) Patent No.: US 10,716,572 B2
(45) Date of Patent: Jul. 21, 2020

(54) BLOOD FLOW REDUCER AND METHOD USING THE SAME

(71) Applicants: Université d'Aix-Marseille, Marseilles (FR); ASSISTANCE PUBLIQUE—HÔPITAUX DE MARSEILLE, Marseilles (FR); INSTITUT NATIONAL DE LA SANTÉ ET DE LA RECHERCHE MÉDICALE, Paris (FR)

(72) Inventors: Pierre Henri Rolland, Marseilles (FR); Vincent Vidal, La Bouilladisse (FR); Emilie Hélène Marie Grégoire, Marseilles (FR)

(73) Assignees: Université d'Aix-Marseille, Marseilles (FR); ASSISTANCE PUBLIQUE—HÔPITAUX DE MARSEILLE, Marseilles (FR); INSTITUT NATIONAL DE LA SANTÉ ET DE LA RECHERCHE MÉDICALE, Paris (FR)

( * ) Notice: Subject to any disclaimer, the term of this patent is extended or adjusted under 35 U.S.C. 154(b) by 249 days.

(21) Appl. No.: 15/559,255

(22) PCT Filed: Mar. 20, 2015

(86) PCT No.: PCT/EP2015/056018
§ 371 (c)(1),
(2) Date: Sep. 18, 2017

(87) PCT Pub. No.: WO2016/150474
PCT Pub. Date: Sep. 29, 2016

(65) Prior Publication Data
US 2018/0085127 A1    Mar. 29, 2018

(51) Int. Cl.
A61B 17/12    (2006.01)

(52) U.S. Cl.
CPC .. *A61B 17/12036* (2013.01); *A61B 17/12009* (2013.01); *A61B 17/12109* (2013.01);
(Continued)

(58) Field of Classification Search
CPC ........ A61B 17/12009; A61B 17/12036; A61B 17/12109; A61B 17/12131;
(Continued)

(56) References Cited

U.S. PATENT DOCUMENTS

2010/0286758 A1    11/2010    Berglund
2013/0096580 A1    4/2013    Cohn et al.
(Continued)

FOREIGN PATENT DOCUMENTS

WO    2004/014474 A1    2/2004

OTHER PUBLICATIONS

International Search Report issued in PCT/EP2015/056018 dated Nov. 4, 2015 (5 pages).
(Continued)

*Primary Examiner* — George J Ulsh
(74) *Attorney, Agent, or Firm* — Osha Liang LLP

(57) ABSTRACT

A blood flow reducer (20) for insertion in a blood vessel, the reducer (20) being adapted to be deformed from a first configuration to an expanded configuration, wherein, in the expanded configuration, the reducer (20) defines an axial lumen (40) for allowing blood flow therethrough, the axial lumen (40) having a smallest cross-section, the reducer (20) has a largest cross-section, and the smallest cross-section is comprised between 20% and 90% of the largest cross-section. In particular, the smallest cross-section is strictly comprised between 70% and 90% of the largest cross-section. A method for preconditioning a liver of a living
(Continued)

being before partial hepatectomy, wherein a 10 to 30% stenosis is created in a branch of a portal vein conducting blood to a first liver lobe.

11 Claims, 4 Drawing Sheets

(52) U.S. Cl.
CPC .. *A61B 17/12131* (2013.01); *A61B 17/12136* (2013.01); *A61B 17/12177* (2013.01); *A61B 2017/1205* (2013.01)

(58) Field of Classification Search
CPC ........ A61B 17/12136; A61B 17/12177; A61B 2017/1205
See application file for complete search history.

(56) References Cited

U.S. PATENT DOCUMENTS

| | | |
|---|---|---|
| 2014/0039537 A1 | 2/2014 | Carrison |
| 2015/0039017 A1 | 2/2015 | Cragg et al. |
| 2015/0066066 A1* | 3/2015 | Cazenave .............. A61B 17/12 606/158 |
| 2017/0303928 A1* | 10/2017 | Cazenave .............. A61B 17/12 |

OTHER PUBLICATIONS

Written Opinion of the International Searching Authority issued in PCT/EP2015/056018 dated Nov. 4, 2015 (7 pages).

E. Gregoire et al.; "Minimal portal vein stenosis is a promising preconditioning in living donor liver transplantaion in porcine model"; Journal of Hepatology, vol. 61, pp. 59-66; 2014 (8 pages).

* cited by examiner

BLOOD FLOW REDUCER AND METHOD USING THE SAME

TECHNICAL FIELD

The present disclosure generally relates to a medical device for reducing the blood flow in a blood vessel, referred to herein as a "blood flow reducer" or simply "reducer", and to a method using the same.

BACKGROUND

The shortage of deceased donor organs compared to the number of patients on the waiting list for liver transplantation requires the use of other sources of grafts. The main hindrance in promoting living donor liver transplantation remains the morbi-mortality risk for the donor.

To reduce this risk, living donor liver preconditioning has been developed to improve the donor postoperative recovery. For example, in 2005, Malik et al. proposed the administration of thyroid hormones T3 to living donors. Accordingly, T3 doses were administered to rats ten days before hepatectomy and an increased total liver volume to body weight ratio was obtained—See "a study relevant to donor preconditioning", Am J Transplant 2005; 5: 1801-1807. However, the administrated doses of T3 (2 mg/kg/day) were nearly 2000 times over the maximum administered dose in humans (2.5 lg/kg/day)—See Hamilton M. et al. "Safety and hemodynamic effects of intravenous triiodothyronine in advanced congestive heart failure", Am J Cardiol 1998; 81: 443-447. Despite these interesting results in terms of liver regeneration, it seems difficult to apply this preconditioning to humans.

Portal vein embolization, as a starter of liver regeneration, has been disclosed, for instance, by Lesurtel M. et al. in "Temporary portal vein embolization as a starter of liver regeneration", J Hepatol 2008; 49: 313-315. In such a technique, a lobar portal vein is occluded so as to induce the atrophy of the ipsilateral liver lobe and, thus, the hypertrophy of the contralateral liver lobe before surgical resection of the ipsilateral liver lobe. Nevertheless, the atrophic consequences of this technique on the ipsilateral liver lobe preclude using this lobe as a liver graft and, therefore, this technique cannot be used in liver preconditioning before liver transplantation.

Thus, there is a need for improved devices and methods for liver preconditioning before partial hepatectomy and, in particular, before liver transplantation.

GENERAL PRESENTATION

According to one aspect of the present disclosure, there is provided a blood flow reducer for insertion in a blood vessel, the reducer being adapted to be deformed from a first configuration to an expanded configuration. In the expanded configuration, the reducer defines an axial lumen for allowing blood flow therethrough, the axial lumen having a smallest cross-section. Still in the expanded configuration, the reducer has a largest cross-section and the smallest cross-section is comprised between 20% and 90% of the largest cross-section.

In some embodiments, in the expanded configuration, the smallest cross-section is strictly comprised between 70% and 90% of the largest cross-section (i.e. the smallest cross-section is strictly larger than 70% and strictly smaller than 90% of the largest cross-section).

In some embodiments, in the expanded configuration, the smallest cross-section is comprised between 75% and 85% (75% and 85% included) of the largest cross-section. In particular, the smallest cross-section is about 80% of the largest cross-section.

The reducer may be inserted percutaneously in said blood vessel in its first configuration. For instance, a delivery catheter is inserted through a central vein and further brought to said blood vessel, through the venous system. The reducer may be released from the delivery catheter in its first configuration and may be allowed to elastically expand and/or be plastically expanded (e.g. using a balloon), thereby adopting its expanded configuration.

The blood vessel may be a portal vein branch and, in particular, a proximal portion of a portal vein branch. The portal vein branch may be the right portal vein branch of an adult human. In humans, immediately before reaching the liver, the main portal vein divides into right and left branches. These (right and left) portal vein branches are also called (right and left) lobar portal veins. The right and left portal vein branches ramify further, forming smaller venous segments and ultimately portal venules. The proximal portion of a portal vein branch, within the meaning of the present disclosure, is the branch portion located between said main portal vein and said venous segments.

In an exemplary embodiment, the largest cross-section of the reducer is adapted to occupy substantially an entire cross-section of a main portal vein or portal vein branch and, in particular, a proximal portion of a portal vein branch (e.g. the right portal vein branch) of an adult human. Thus, the largest cross-section of the reducer may be substantially circular, so as to fit with the cross-section of the portal vein branch. For the purpose of the present disclosure a cross-sectional dimension shall be understood as a linear dimension measured across a cross-section. In particular, the skilled person will readily recognize that this is the diameter of a circular cross-section.

The reducer may be provided in a variety of gauges (e.g. different largest cross-section, different smallest cross-section, different ratios between the largest and the smallest cross-sections), thus providing the physician with the ability to select an appropriate reducer for the patient from a set of available sizes. In particular, a set of reducer of different sizes may be provided to a physician for surgery.

In some embodiments, the reducer comprises a tubular member with an inner surface defining the axial lumen and the axial lumen comprises at least one narrow region and at least one flared region. The flared region is located between the narrow region and an axial end of the tubular member. The smallest cross-section of the axial lumen is located in the narrow region. When the tubular member is formed by a thin tubular wall, the largest cross-section of the reducer substantially corresponds to the largest cross-section of the axial lumen.

For instance, the reducer may comprise a central narrow region and two flared regions, one on each side of the central narrow region. In particular, the reducer may be diabolo-shaped. It may have rotational symmetry about a central axis and reflection symmetry about a median plan of the central narrow region, orthogonal to the central axis.

Alternatively, the reducer may be asymmetric.

In some embodiments, the largest cross-section is located at an axial end of the tubular member. In particular, the reducer may comprise a rim at its axial end and the rim may define the largest cross-section. The rim may be constructed to be more difficult to expand (for a plastically deformed reducer) or expand less (for a self-expanding reducer) than portions of the reducer just inside the rim, thereby preventing over expansion of the reducer.

In some embodiments, the tubular member is coated with a flexible coating (inside and/or outside) and/or defines a dense mesh pattern that prevents or reduces blood flow through the wall of the tubular member. Therefore, the entire blood flow, or most of it, passes through the axial lumen of the tubular member. For instance, the tubular member may comprise a mesh structure coated with a flexible waterproof coating.

The above-described blood flow reducer may be used for liver preconditioning before partial hepatectomy (i.e. before surgical resection of a part of the liver) and, in particular, before major hepatectomy (i.e. a resection of three or more liver segments).

The reducer may be used for creating a stenosis in the portal vein branch conducting blood to a first liver lobe, the stenosis triggering regeneration in the contralateral liver lobe. The liver preconditioning thus comprises the regeneration of the contralateral liver lobe (i.e. the remnant liver lobe, after resection) before surgical resection of the first liver lobe.

The reducer can also be used in the preparation of major hepatectomy with the advantage of not burning bridges to a change in surgical strategy, or in the management of bilobar liver metastases by sequential hepatectomy. In this case, the reducer indications are comparable to those of the reversible portal vein embolization with the major advantage of not inducing atrophy downstream the portal stenosis.

The reducer may further be used in the treatment of post hepatectomy liver failure, in order to reduce portal overflow and small for size syndrome. In this case, the expected vessel cross-section reduction is comprised between 50 and 80% of the initial diameter of the main portal vein, in order to reduce portal blood flow in normal range.

In case of living donor preconditioning, the reducer may be inserted in the proximal portion of the portal vein branch of the future graft, in order to induce the hypertrophy of the future remnant liver of the donor before hepatectomy. In case of sequential hepatectomy, the reducer will be inserted in the proximal portion of the portal vein branch on the side of the hepatectomy, in order to induce the hypertrophy of the future remnant liver before hepatectomy. In case of treatment of post hepatectomy liver failure, the reducer will be inserted in the main portal vein.

According to another aspect of the present disclosure, there is provided a method for preconditioning a liver of a living being before partial hepatectomy, wherein a 10 to 30% stenosis is created in a branch of a portal vein conducting blood to the first liver lobe. A 10 to 30% stenosis, within the meaning of the present disclosure, means that the flow section of the portal vein branch is reduced by more than 10% (10% excluded) and less than 30% (30% excluded). In particular, a 15 to 25% stenosis may be created, 15% and 25% being included, and the stenosis may be around 20%.

After the preconditioning, at least one part of the first liver lobe and/or at least one part of a contralateral liver lobe may be resected. In particular, a major hepatectomy (i.e. a resection of three or more liver segments) can be performed.

In particular, the first liver lobe may be resected and transplanted. The proposed method may thus be used for preconditioning the liver of a living human donor, before transplantation.

Alternatively, the resected part of the first and/or contralateral liver lobe may be, for instance, a tumorous part.

The first liver lobe may be the right lobe of a human liver.

The above-described stenosis may by created by using the above-described blood flow reducer. However, other kinds of medical devices could be used. In particular, devices such as stripes, bands, ties, rings, collars etc. could be used to create the stenosis by clamping the portal vein branch.

The blood flow reducer may be removed from the portal vein branch through endovascular surgery. In particular, it may be removed after the surgical resection or before, when the surgical resection is cancelled or postponed.

Other features and advantages of the invention will become apparent from the following detailed description, taken in conjunction with the accompanying drawings, which illustrate, by way of example, some principles of the invention.

BRIEF DESCRIPTION OF THE DRAWINGS

In the drawings, like reference signs generally refer to the same or like parts throughout the different views.

The drawings are not necessarily to scale, emphasis instead generally being placed upon illustrating some principles of the invention.

DETAILED DESCRIPTION

In the following detailed description, it is referred to the accompanying drawings showing examples of blood flow reducers and liver preconditioning methods. It is intended that these example be considered as illustrative only, the scope of the invention not being limited to these examples.

For the sake of conciseness, the description may omit certain information known to those skilled in the art and, thus, unnecessary for them to practice the invention.

Results of liver preconditioning based on moderate changes in the portal venous blood flow in a porcine model, and their consequences on hepatic remodeling, are first reported below.

[Materials and Methods]
[Animal Model]

Figure 1:
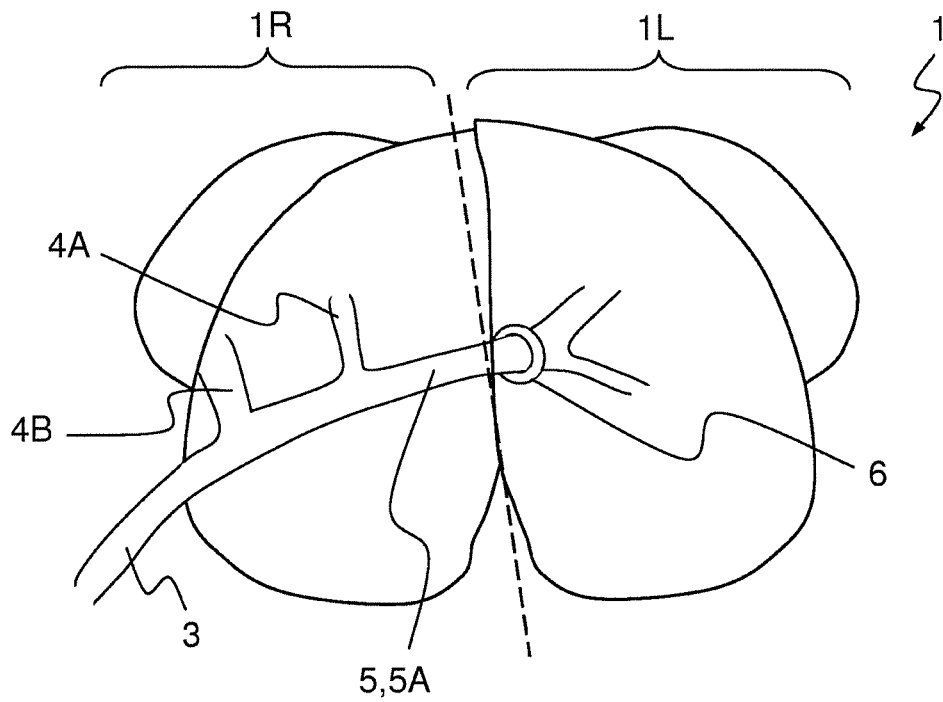
FIG. 1 is a diagrammatic view of a porcine liver, with a tie tightened on the left portal vein branch.

Because of its similarities in terms of human anatomy and hepatic metabolism, the porcine model has been chosen to illustrate the advantages of the invention. However, while in the human liver, the main portal vein generally has a unique right portal vein branch (as detailed hereafter and illustrated in FIGS. 2-3), in the porcine liver 1, as illustrated in FIG. 1, the porcine main portal vein 3 is divided in two branches 4A, 4B for the right liver lobe 1R, which immediately penetrate in the liver parenchyma making them very difficult to control. The porcine left portal vein branch 5, however, is unique and includes a proximal portion 5A of a few centimeters which is easy to control. As the right and the left porcine liver lobes 1R, 1L are of equivalent size, it was decided to reverse the human model using the right liver lobe 1R as the future remnant liver lobe of the donor and the left liver lobe 1L as the future graft in the porcine model.

[Animals]

Twenty four, six-month-old pigs (Pietrin), weighting 40 to 50 kg were used for these studies. After a 5-days period of acclimatization, all surgical procedures or samples procurements were performed between 8:00 AM and 12:00 AM. The experiments were terminated by intravenous injection of 15 mg midazolam and 25 mg chlorpromazine in 20 ml KCl (15%). The experiments described in this study were conducted according to the European Convention for the Protection of Vertebrate Animals used for Experimental and Other Scientific Purposes and after approval of the Ethical Committee of Provence.

[Phase A—Hemodynamics Study]

Six pigs were fasted 12 h before surgery with free access to water. After sedation by 30 mg/kg ketamine and 0.03 mg/kg acetopromazin, a venous catheter was inserted in a large vein in the ear for initial blood sampling and intravenous administrations. Induction of anesthesia was obtained by 2 mg/kg propofol. Anesthesia was maintained with gaseous sevoflurane (1.2%) by mechanical respiration (Zeus Dräger Inc.) and constant intravenous infusion of sufentanil (1 lg/kg/hour). Hemodynamic measurements was were carried as previously described in details in: Rolland PH et al. "Compliance matching stent placement in the carotid artery of the swine promotes optimal blood flow and attenuates restenosis" Eur J Vasc Endovasc Surg 2004, 28, 431-438; Berry J et al. "Hemodynamics and wall mechanics of a compliance matching stent: in vitro and in vivo analysis" J Vasc Interv Radiol 2002, 13, 97-105; and Mekkaoui C et al. "Pressure-flow loops and instantaneous input impedance in the thoracic aorta: another way to assess the effect of aortic bypass graft implantation on myocardial, brain, and subdiaphragmatic perfusion" J Thorac Cardiovasc Surg 2003, 125, 699-710.

Briefly, a midline abdominal incision was performed and ultrasound transit time flowmeter probes were positioned around the portal vein, the left portal vein and the hepatic artery for continuous measurement of blood flow (20, 7, and 3 RS probes, Transit Time Flow Meter, Transonic, Ithaca, N.Y., USA). Pressure-measurement catheters were placed into the main portal vein and the hepatic artery downstream of the flowmeter probes so as not to disturb flow measurements. Piezoelectric sensors were placed around the portal vein and the hepatic artery next to the flowmeter probes for continuous measurement of vessel diameter. All probes and sensors were recorded on a multichannel LabView based PXi system (National Instrument).

Then, a portal vein band was placed around the left portal vein upstream of the flowmeter probe including an external rigid ring (polypropylene) and an internal inflatable balloon (silicone) in order to progressively reduce left portal flow. The "Zero" calibration was checked for each animal. All parameters were recorded simultaneously, a 15 min stabilization, under basal conditions and after each left portal flow modification during 15 min. The balloon was inflated milliliter by milliliter and the degree of the stenosis was verified on successive portography in order to obtain 10, 20, 30, 50, 60, 65, 70, 75, 80, 90, and 100% left portal vein stenosis (abbreviated to LPV stenosis). At the end of the experiments, the animals were euthanized.

[Phase B—Biological, Cellular and Molecular Consequences of LPV Stenosis]

[Surgery and Samples Collection]

Twelve pigs were divided in 4 groups: sham operated animals (group 0, n=3), 20% LPV stenosis (group 20, n=3), 50% LPV stenosis (group 50, n=3), and 100% LPV stenosis (group 100, n=3). In each group, the animals were anesthetized as described above. In each animal, the left portal vein was isolated (day 0). Deep Liver biopsies were performed on the right and left lobes and blood samples were collected. The circumference of the left portal vein was directly measured by passing a silk thread around the vessel. As illustrated in appended FIG. 1, a non-stretch stripe of polypropylene 6 whose length was calculated to induce a 20, 50 or 100% stenosis was sewed around the left portal vein 5. Sham operated animals underwent only portal dissection and basal portography. Every day, from day 1 to day 5, animals were anesthetized (ketamine 1 mg, acepromazine 10 mg, IM). Blood samples and US-guided percutaneous deep liver biopsies from the left lateral lobe and the right lateral lobe were collected (Needle core biopsy BARD, 18 G). At day 7 animals were euthanized and the whole liver was removed, weighted, and separated into left liver segments and right liver segments.

[Samples Analysis]

[Biological Consequences of LPV Stenosis]

Serum alanine aminotransferase (ALAT), aspartate aminotransferase (ASAT), gamma-glutamyltransferase (GGT), alkaline phosphatase (ALP) and total bilirubin (TB) were measured with the biochemical multi-analyser in the hospital biochemistry department. Prothrombin time was measured with STA-R (diagnostic stago Asniere France) in the hospital hematology department.

[Results]

[Hemodynamic Study According to an Increasing LPV Stenosis]

No significant modification of hemodynamic parameters (blood flow, blood pressure and diameter in the main portal vein, left portal vein and hepatic artery (HA) when a 10% left portal vein stenosis was applied compared to basal conditions. A 20% left portal vein stenosis induced a significant vasodilation ($p<0.05$) of the HA within 75 seconds and a significant increase ($p<0.05$) in HA blood pressure and blood flow. In the same time, blood flow in the LPV decreased from 0.40±0.09 L/min (basal LPV flow) to 0.33±0.06 L/min. A decrease in LPV pulsatility was also noted downstream of the stenosis since the ratio of minimum to peak LPV blood flow (pulse) decreased from 0.16±0.03 L/min to 0.05±0.01 L/min. The hemodynamic profile of the hepatic artery after a 20% LPV stenosis showed a four-fold increased arterial blood flow whereas the level of arterial blood pressure was comparable to that obtained after a 100% LPV stenosis. There was no statistical difference in hemodynamic changes from 50% to 100% LPV stenosis. No significant modification of the blood flow in the portal trunk during the increase of left portal vein stenosis was observed.

[Biological, Cellular, and Molecular Consequences of LPV Stenosis]

[Effect of LPV Stenosis on Liver Biology]

No significant difference was observed between groups 0, 20, 50, and 100 in serum transaminase levels. There was no modification in daily measurement of prothrombin time, ALP, and TB in each group and between the different groups. Serum level of GGT increased progressively from day 1 (40±10 IU/L) to day 4 (104±20 IU/L) in the group 100 but did not show any significant modification in other groups.

[Measurement of Cell Proliferation following LPV Stenosis: Ki67 Proliferation Index]

For cell proliferation, Ki67 immunohistochemistry using MIB-1 antibody was performed on 5-micron-liver sections formalin-fixed, paraffin-embedded (FFPE) tissues from right and left liver daily biopsies. The Leica BOND-III fully automated IHC stainer was used with high-efficiency de-waxing processes, EDTA-based Ag unmasking procedures and IHC with appropriate NovoCastra antibodies and final DAB-horseradish peroxidase stainings and hematoxylin counterstaining. Proliferation index was determined by the percentage of cells that display nuclear staining reported to the total number of nuclei (ten fields per slide, 400×).

For nuclear density and lobar area, morphometric analysis were performed using the Nikon Eclipse Ni H600L microscopic and image analysis systems.

Three days after surgery, 20% LPV stenosis triggered a significant cell proliferation in the right liver with peak of proliferation at day 5 (44% of cells that displayed nuclear staining for Ki67; p=0.019). There was no significant difference in the intensity of the proliferative activity in right liver after 20 or 100% LPV stenosis (p=0.65).

[Effect of LPV Stenosis on Hepatocyte Size in the Ligated Liver]

There was no difference in the hepatocyte nuclear density or the lobular area in the left liver of the Group 0 and 20 at day 5. Contrariwise, the nuclear density was significantly increased and the hepatocyte lobular area was decreased in the left liver of the group 50 and 100 which indicates a significant atrophy in the left liver in these groups 5 day after surgery.

[Molecular Consequences]

The analysis of molecular markers of atrophy (autophagy and apoptosis) and liver regeneration (STAT3) demonstrated that there was no atrophy in the left liver in group 0 and 20 whereas there was a significant enhancement of autophagy (LC3-II) and apoptosis (activated Caspase 3) in the left liver after 50% and 100% LPV stenosis. The analysis of STAT3 confirmed that liver regeneration was intensively initiated in the right liver one day after surgery in the Group 20.

[Hepatic Remodeling after 20% LPV Stenosis]

[Effect of LPV Stenosis on Right and Left Liver Proportions (Phase B)]

In sham operated animals (group 0), right and left liver were of equivalent size that is the right liver represented 53±2.9% of the total liver weight and the left liver 47±2.8%. In group 20, the proportions of the left and right livers were respected and there was no left liver atrophy (p=0.73). Inversely, we noted a significant atrophy of the left liver after a 50% and 100% LPV stenosis. The left liver in the group 50 and the group 100 represented only 36±4.5 and 32±10.4% respectively of total liver weight 7 days after surgery (p=0.05). The proportion of the left liver in the group 50 was significantly smaller than in the group 20 (p=0.04).

[Hepatic Volumetry (Phase C)]

Six pigs were used for this phase. All animals were weighed 3 days before and 14 days after surgery. An abdominal CT scan was performed for each animal under general anesthesia, 3 days before (i.e. day −3) and 11 days after surgery (i.e. day 11). The apparatus used was a veterinarian scanner monobaret (Cabassu Clinic, Marseille) of the General Electric Company (GE). The acquisition was started 80 s after the IV injection of iodinated contrast (50 ml Telebrix). Three millimeters slides were done every 2 mm. Volumetric reconstruction was performed using the ADW server software (GE). Surgical procedure was similar to the Phase B. The animals were divided into 2 groups: a "test" group with a 20% LPV stenosis (n=3) and a control group (n=3), consisting of 2 sham operated animals (=Group 0) and an animal with a ligature of the LPV (=Group 100). The animals were euthanized 14 day after surgery.

In groups 0 and 20, the volume of the left lobe varied little between day 11 and day −3 while there was an obvious atrophy of the left lobe after ligation of the LPV (group 100). In group 0, the volume of the right lobe varied little between day 11 and day −3 while in the groups 20 and 100, hypertrophy of the right lobe was observed 11 days after preconditioning. This was confirmed by analyzing the total liver volume to body weight ratio at day −3 and day 11. At day 0, the total liver volume to body weight ratio was 2.6 for group 0; 2.5 in group 20, and 2.3 for the group 100. At day 11, the 20% LPV stenosis preconditioning was responsible for an increase of the total liver volume and in the total liver volume to body weight ratio, while this ratio remained stable in the groups 0 and 100.

CONCLUSION

The mechanistic approach of hemodynamic changes following a progressive left portal vein (LPV) stenosis identified a 10% LPV stenosis as the excluded lowest limit for triggering the mechanisms of maintenance of the hepatic blood flow, while a 20% LPV stenosis provides good results.

The cellular study shows that a 20% LPV stenosis preconditioning triggers the liver regeneration in the contralateral lobe (the future remnant liver of the donor) with cell proliferation (Ki67) equivalent to that observed after ligation of the left portal vein. In addition, there is no cellular atrophy downstream of the 20% LPV stenosis (future graft).

The molecular study confirms the trigger of liver regeneration 24 h after the 20% LPV stenosis preconditioning (STAT3) in the future remnant liver of the donor. The absence of atrophy downstream the 20% LPV stenosis was confirmed by the absence of the autophagy (LC3-II) and apoptosis (activated caspase 3) markers.

Finally, the study of changes in liver volume secondary to the 20% LPV Stenosis, is the clinical confirmation of the effectiveness of the preconditioning, i.e., an increase in total liver volume, total liver volume to body weight ratio and the absence of the future graft atrophy.

Thus the 20% LPV stenosis is identified as a good example of effective preconditioning able to prepare the liver of the donor to major hepatectomy without altering the future graft.

[Examples of Medical Devices]

Examples of medical devices capable to create a portal vein stenosis are now described.

Figure 2:
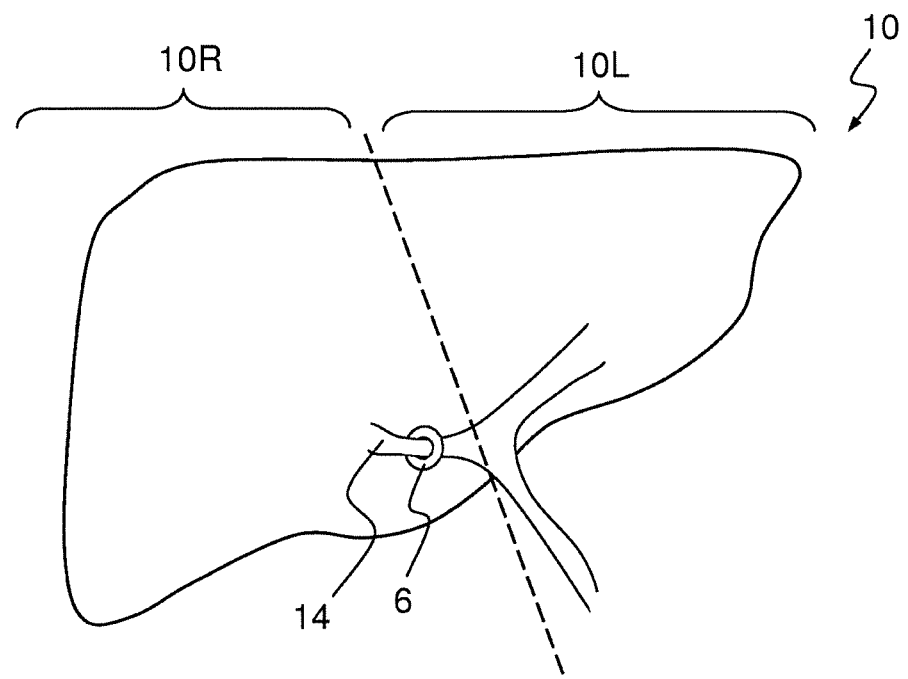
FIG. 2 is a diagrammatic view of a human liver, with a tie tightened on the right portal vein branch.

FIG. 2 illustrates a human liver 10 with a right liver lobe 10R and a left liver lobe 10L. A non-stretch stripe 6 (like the one shown in FIG. 1) is positioned around the right portal vein (abbreviated to "PV") branch 14 of a human liver 10. The length of the stripe 6 may be calculated to induce the desired stenosis and the stripe 6 may be sewed around the right PV branch 14. Of course, other kinds of stripes, bands, ties, rings, collars etc. could be used to clamp the PV branch 14 and reduce its flow section.

Figure 3:
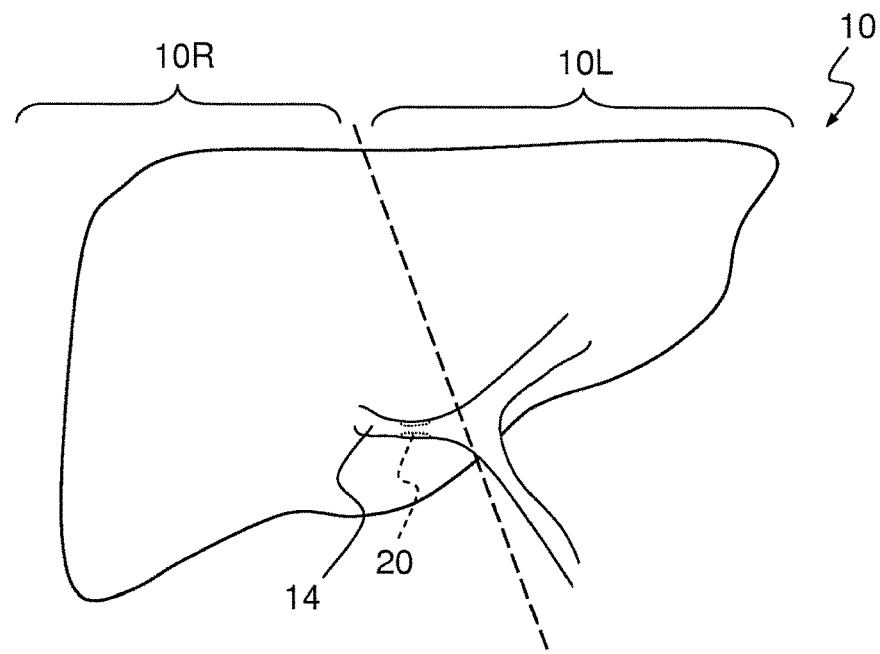
FIG. 3 is a diagrammatic view of a human liver, with a blood flow reducer in the right portal vein branch.

FIGS. 4 to 9 show examples of endovascular blood flow reducers 20 which can be used to create a portal vein stenosis. In the figures, the reducers 20 are shown in their expanded configuration. The reducers 20 can adopt a first configuration (not shown), more compact than their expanded configuration. The reducers 20 are brought, in their first configuration, to the proximal portion of the right PV branch 14 of a human liver 10 through endovascular surgery. Once the reducer 20 is brought to the portal vein (abbreviated to "PV") branch 14 and has reached its expanded configuration, as illustrated in FIG. 3, the blood flow in the PV branch 14 decreases due to the flow section reduction. The reducers 20 may be self-expanding.

Figure 4:
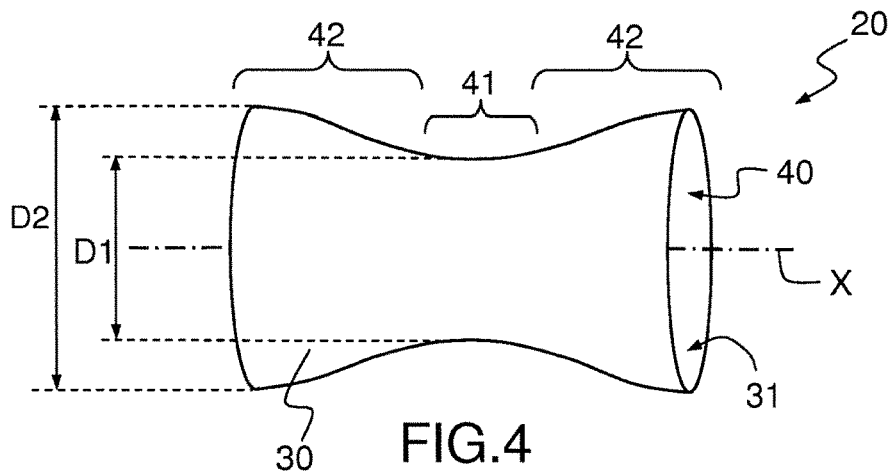
FIG. 4 is a diagrammatic view of a first example of a blood flow reducer.
Figure 5:
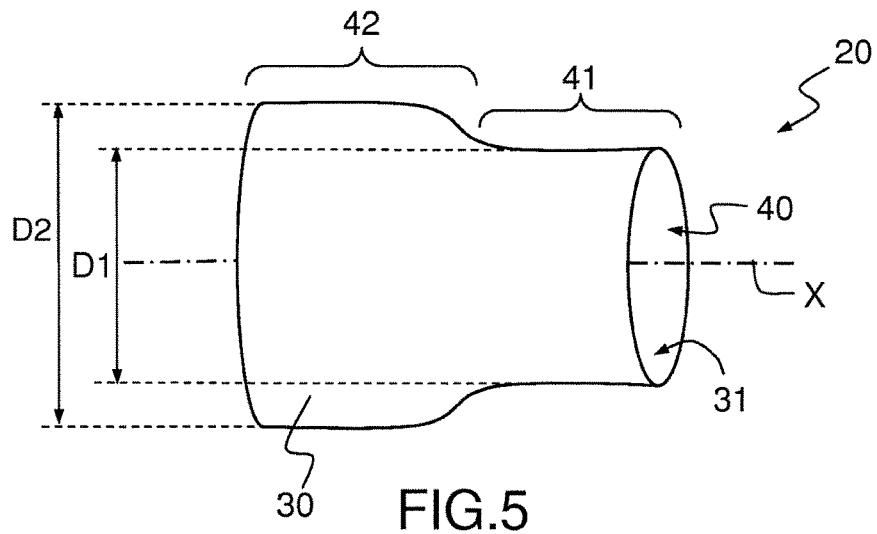
FIG. 5 is a diagrammatic view of a second example of a blood flow reducer.

The reducers 20 of FIGS. 4 to 8 comprise a tubular member 30 with an inner surface 31 defining an axial lumen 40. The axial lumen 40 comprises a narrow region 41 and at least one flared region 42. The smallest cross-section of the axial lumen 40 is circular, with a diameter D1, and located in the narrow region 41. The largest cross-section of the reducer 20 is circular with a diameter D2. In the examples of FIGS. 4-5, the tubular member 30 is formed by a thin tubular wall and the cross-section of the tubular wall 30 varies along its central axis X. Because the wall of the tubular member 30 is very thin compared to the cross-sectional dimensions of the tubular member 30, the largest cross-section of the reducer 20 substantially corresponds to the largest cross-section of the axial lumen 40.

In FIG. 4, the reducer 20 is diabolo-shaped: it comprises a central narrow region 41 and two flared regions 42, one on each side of the central narrow region 41. It has rotational symmetry about the central axis X and reflection symmetry about a median plan of the central narrow region 41, orthogonal to the central axis X.

In FIG. 5, the reducer 20 is asymmetric and comprises one narrow region 41 and one flared region 42.

Figure 6:
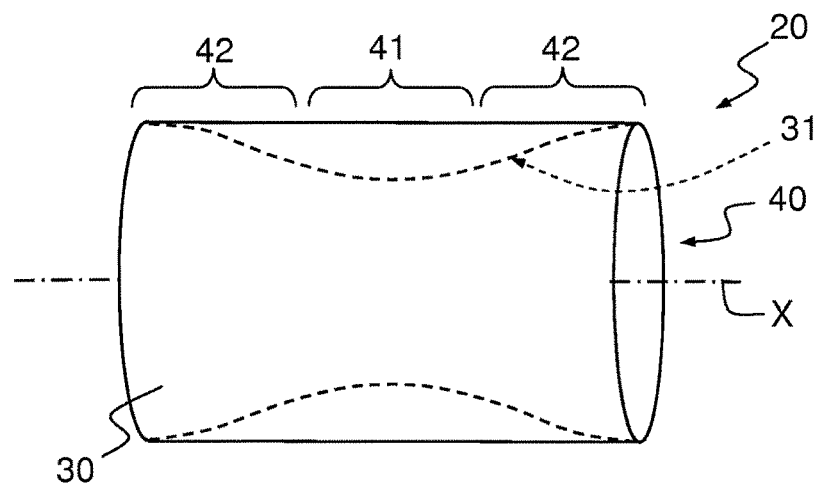
FIG. 6 is a diagrammatic view of a third example of a blood flow reducer.
Figure 7:
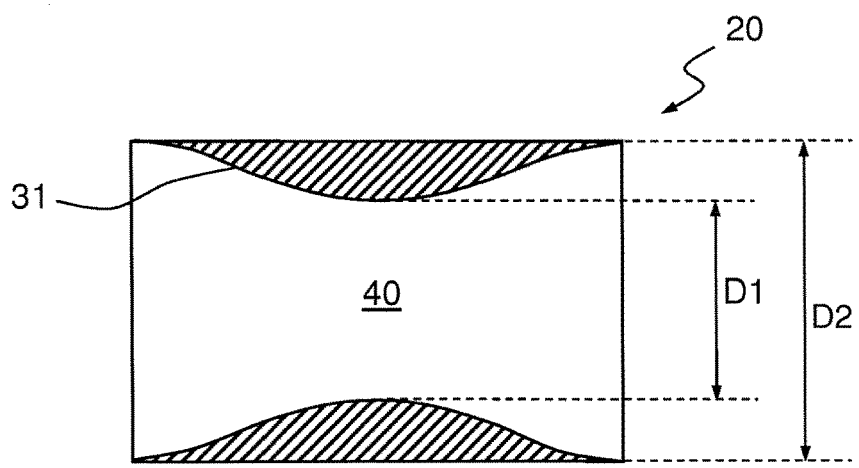
FIG. 7 is a sectional view, in an axial plane, of the blood flow reducer of FIG. 6.

The reducer of FIGS. 6-7 comprises a tubular member 30 with a constant circular cross-section of diameter D2. The inner surface 31 of the tubular member 30 defines an axial lumen 40. The tubular wall of the tubular member 30 has a varying thickness and, thus, the cross-section of the axial lumen 40 varies along the central axis X. The axial lumen 40 comprises a central narrow region 41 and two flared regions 42, one on each side of the central narrow region 41.

Figure 8:
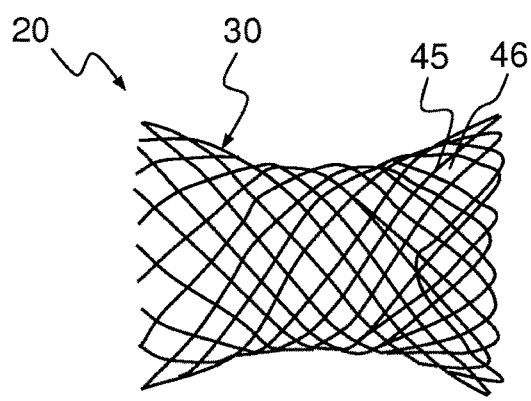
FIG. 8 shows another example of a blood flow reducer.

FIG. 8 illustrated an example of reducer 20 comprising a tubular member 30 formed by a mesh structure 45 coated with a flexible layer 46 forming a waterproof cover around the mesh structure 45. The mesh structure 45 may be metallic (e.g. an alloy of nickel and titanium such as nitinol) and the layer 46 may be polymeric (e.g. in PTFE).

Figure 9A:
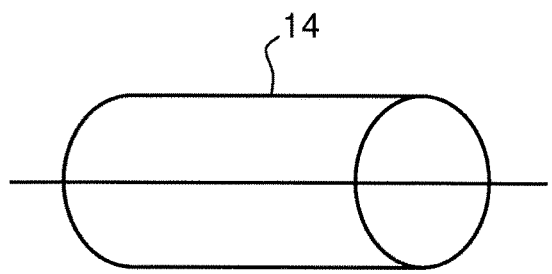
FIGS. 9A to 9E illustrate different steps of the installation of another example of a blood flow reducer.
Figure 9B:
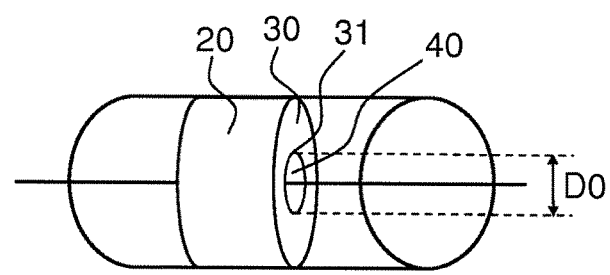
Figure 9C:
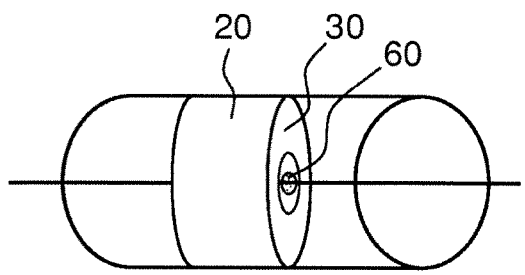
Figure 9D:
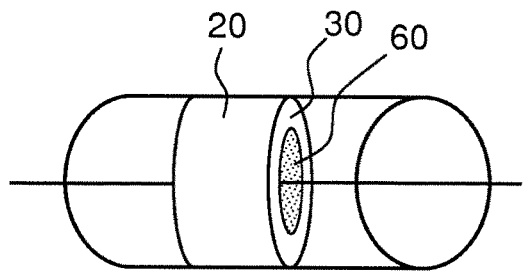
Figure 9E:
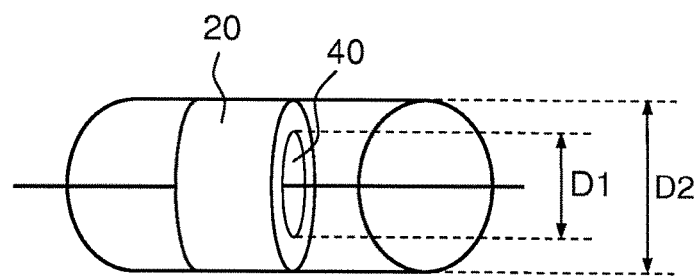

FIGS. 9A to 9E illustrate different steps of the installation of another example of a blood flow reducer 20. The reducer 20 comprises a tubular member 30 with an inner surface 31 defining an axial lumen 40. FIG. 9A illustrates a portion of a PV branch 14 where the reducer is to be inserted. The reducer is brought to the PV branch in a first configuration, illustrated in FIG. 9B where the axial lumen 40 has a cross-section of diameter D0. Then, an inflatable balloon 60 is inserted in the axial lumen, as shown in FIG. 9C. When the balloon 60 is inflated, it enlarges the cross-section of the axial lumen 40 towards the desired cross-section having the diameter D1 (expanded configuration). The balloon is then removed.

The cross-section of diameter D1 is the cross-section of the axial lumen 40 in the expanded configuration. In the illustrated example, this cross-section is constant and, therefore, corresponds to the smallest cross-section of the axial lumen 40. The largest cross-section of the reducer 20 has a diameter D2 (the largest cross-section is substantially the same in the first and expanded configurations).

All the blood flow reducers 20 of FIGS. 4 to 9 are configured so that, in their expanded configuration, the smallest cross-section of diameter D1 is comprised between 20 and 90% and, in particular, strictly comprised between 70% and 90% of the largest cross-section of diameter D2, i.e. $70\% \times Pi \times (D2 \times \frac{1}{2})^2 < Pi \times (D1 \times \frac{1}{2})^2 < 90\% \times Pi \times (D2 \times \frac{1}{2})^2$, where Pi is the mathematical constant commonly approximated as 3.14159.

In understanding the scope of the invention, the term "comprise" and its derivatives, as used herein, will be understood as open ended terms implying the presence of the stated feature(s), element(s), component(s), and/or step(s), but not excluding the presence of any other unstated feature(s), element(s), component(s) and/or step(s). The foregoing also applies to words having similar meanings such as "include", "have" and their derivatives. The terms of degree such as "substantially", "about" and "approximately" as used herein mean a reasonable amount of deviation of the modified term such that the end result is not significantly changed.

While only selected embodiments have been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature which is unique from the prior art, alone or in combination with other features, also should be considered a separate description of further inventions by the applicant, including the structural and/or functional concepts embodied by such features. Thus, the foregoing descriptions of the embodiments according to the present invention are provided for illustration only, and not for the purpose of limiting the invention as defined by the appended claims.

The invention claimed is:

1. A method for preconditioning a liver of a living being before partial hepatectomy, wherein a 10 to 30% stenosis is created in a branch of a portal vein conducting blood to a first liver lobe; wherein the stenosis is created by using a blood flow reducer for insertion in the portal vein branch, the blood flow reducer being adapted to be deformed from a first configuration to an expanded configuration, wherein, in the expanded configuration, the reducer defines an axial lumen for allowing blood flow therethrough, the axial lumen having a smallest cross-section, wherein the blood flow reducer has a largest cross-section adapted to occupy substantially an entire cross-section of the portal vein branch; and wherein the smallest cross-section is strictly comprised between 70% and 90% of the largest cross-section; wherein the blood flow reducer comprises a tubular member with an inner surface defining the axial lumen, wherein the axial lumen comprises at least one narrow region and at least one flared region, the flared region being located between the narrow region and an axial end of the tubular member, and the smallest cross-section being located in the narrow region.

2. The method of claim 1, wherein at least one part of the first liver lobe and/or at least one part of a contralateral liver lobe is resected.

3. The method of claim 2, wherein the first liver lobe is resected and transplanted.

4. The method of claim 2, wherein the resected part is a tumorous part.

5. The method of claim 1, wherein the first liver lobe is a human liver lobe.

6. The method of claim 1, wherein the entire cross-section is the entire cross-section of a proximal portion of the portal vein branch of an adult human.

7. The method of claim 1, wherein the smallest cross-section is comprised between 75% and 85% of the largest cross-section.

8. The method of claim 1, wherein the smallest cross-section is about 80% of the largest cross-section.

9. The method of claim 1, wherein the largest cross-section is located at the axial end of the tubular member.

10. The method of claim 1, wherein the tubular member is coated with a flexible coating and/or defines a dense mesh pattern that prevents or reduces blood flow through the wall of the tubular member.

11. The method of claim 1, wherein the blood flow reducer is removed from the portal vein branch through endovascular surgery.

* * * * *